United States Patent [19]

Hofer et al.

[11] 4,010,157
[45] Mar. 1, 1977

[54] O-ALKYL-S-[1,6-DIHYDRO-3-METHYL-6-OXO-PYRIDAZIN-(1)-YLMETHYL](THIONO) (DI)THIOL-PHOSPHORIC ACID ESTERS AND ESTER-AMIDES

[75] Inventors: Wolfgang Hofer; Fritz Maurer; Hans-Jochem Riebel; Lothar Rohe, all of Wuppertal; Bernhard Homeyer, Opladen, all of Germany

[73] Assignee: Bayer Aktiengesellschaft, Leverkusen, Germany

[22] Filed: Sept. 13, 1974

[21] Appl. No.: 505,801

[30] Foreign Application Priority Data

Sept. 28, 1973 Germany .......................... 2348736

[52] U.S. Cl. .......................... 260/250 AP; 424/250
[51] Int. Cl.² .......................... C07F 9/24
[58] Field of Search .............. 260/250 AP

[56] References Cited

UNITED STATES PATENTS 2,938,902 5/1960 DuBreuil .............. 260/250 AP

*Primary Examiner*—Donald G. Daus
*Assistant Examiner*—Mark L. Berch
*Attorney, Agent, or Firm*—Burgess, Dinklage & Sprung

[57] ABSTRACT

O-alkyl-S-[1,6-dihydro-3-methyl-6-oxo-pyridazin-(1)-ylmethyl](thiono) (di)thiol-phosphoric acid esters and ester-amides of the formula

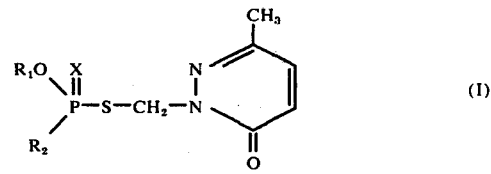

in which
  $R_1$ is alkyl with up to 6 carbon atoms,
  $R_2$ is alkylmercapto, monoalkylamino, dialkylamino, alkenylamino or alkynylamino with up to 6 carbon atoms per alkyl, alkenyl or alkynyl moiety, and
  X is oxygen or sulfur, which possess nematocidal, insecticidal, acaricidal and fungicidal properties.

6 Claims, No Drawings

O-ALKYL-S-[1,6-DIHYDRO-3-METHYL-6-OXO-PYRIDAZIN-(1)-YLMETHYL](THIONO) (DI)THIOL-PHOSPHORIC ACID ESTERS AND ESTER-AMIDES

The present invention relates to and has for its objects the provision of particular new O-alkyl-S-[1,6-dihydro-3-methyl-6-oxo-pyridazin-(1)-ylmethyl] (thiono) (di)thiol-phosphoric acid esters and ester-amides, i.e., O-alkyl-S-alkyl-S-[1,6-dihydro-3-methyl-6-oxo-pyridazin-(1)-ylmethyl]-dithiol-phosphoric acid esters, O-alkyl-N-alkyl-, -N,N-dialkyl-, -N-alkenyl- or -N-alkynyl-S-[1,6-dihydro-3-methyl-6-oxo-pyridazin-(1)-ylmethyl] thiolphosphoric acid ester-amides and their thiono counterparts, which possess nematocidal, insecticidal, acaricidal and fungicidal properties, active compositions in the form of mixtures of such compounds with solid and liquid dispersible carrier vehicles, and methods for producing such compounds and for using such compounds in a new way especially for combating pests, e.g. nematodes, insects, acarids and fungi, with other and further objects becoming apparent from a study of the within specification and accompanying examples.

It has been disclosed in German Published Specifications DAS No. 1,106,766 and DOS No. 2,006,020 that certain S-[1,6-dihydro-3-methyl-6-oxo-pyridazin-(1)-ylmethyl]-thiono-thiol-phosphoric(phosphonic) acid esters, for example S-[1,6-dihydro-3-methyl-6-oxo-pyridazin-(1)-ylmethyl]-O,O-diethyl-thiono-thiol-phosphoric acid ester (Compound A) and -o-ethyl-thiono-thiol-ethanephosphonic acid ester (Compound B), exhibit insecticidal, acaricidal and nematocidal properties.

The present invention provides S-[1,6-dihydro-3-methyl-6-oxo-pyridazin-(1)-ylmethyl]-(thiono)-(di)-thiol-phosphoric acid ester and ester-amide derivatives of the formula

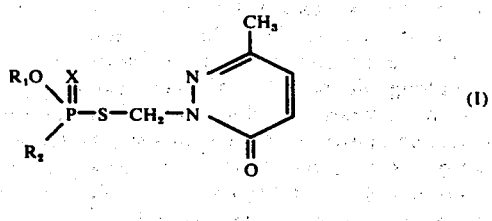

in which
  $R_1$ is alkyl with up to 6 carbon atoms,
  $R_2$ is alkylmercapto, monoalkylamino, dialkylamino, alkenylamino or alkynylamino with up to 6 carbon atoms per alkyl, alkenyl or alkynyl moiety, and
  X is oxygen or sulfur.

Preferably, $R_1$ represents straight-chain or branched lower alkyl with up to 4 carbon atoms, especially ethyl, n-propyl or isopropyl, and $R_2$ represents straight-chain or branched lower alkylmercapto, mono-lower alkylamino, di-lower alkylamino, lower alkenylamino or lower alkynylamino with up to 4 carbon atoms per lower alkyl, alkenyl or alkynyl moiety.

Surprisingly, the S-[1,6-dihydro-3-methyl-6-oxo-pyridazin-(1)-ylmethyl]-(thiono)-(di)-thiolphosphoric acid ester and ester-amide derivatives according to the invention have a substantially better nematocidal action than the previously known compounds of analogous structure and of the same type of action. The compounds according to the invention thus represent a genuine enrichment of the art.

The invention also provides a process for the production of an S-[1,6-dihydro-3-methyl-6-oxo-pyridazin-(1)-ylmethyl]-(thiono)-(di)-thiol-phosphoric acid ester or ester-amide derivative of the formula (I) in which a 1,6-dihydro-1-halomethyl-3-methyl-6-oxo-pyridazine of the general formula

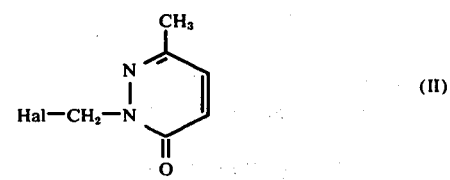

in which
  Hal represents halogen
is reacted with a salt of a (thiono)-(di)thiolphosphoric acid ester or ester-amide of the general formula

in which
  M represents an alkali metal, alkaline earth metal or ammonium equivalent, and
  $R_1$, $R_2$ and X have the abovementioned meanings.

Preferably, Hal represents chlorine and M represents sodium or potassium.

If, for example, 1,6-dihydro-1-chloromethyl-3-methyl-6-oxo-pyridazine and the potassium salt of O-methyl-S-ethyl-thionodithiolphosphoric acid ester are used as starting materials, the course of the reaction can be represented by the following formula scheme:

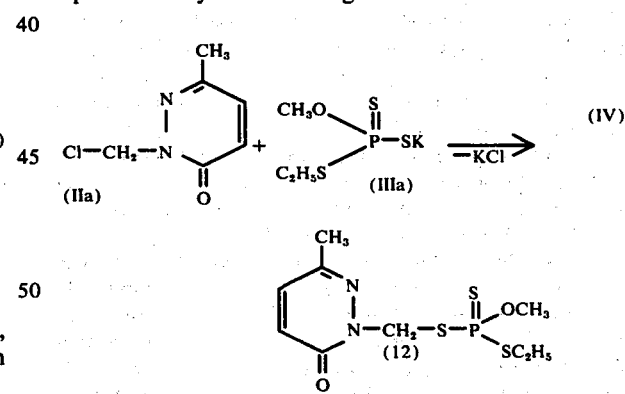

The 1-halomethyl-3-methyl-6-oxo-pyridazines of the formula (II) are known and can be prepared according to known customary methods as set forth in German Published Specification DOS No. 2,006,020.

The salts of the (thiono)-(di)thiolphosphoric acid esters and ester-amides (III) are in most cases known. They can be prepared according to customary methods as set forth in German Published Specification DOS No. 2,035,073 and Houben-Weyl "Methoden der Organischen Chemie" ("Methods of Organic Chemistry"), volume 12/2; page 754, by treating the corresponding ester-halides or ester-amide-halides (V) with hydrogen sulfide in the presence of carbonates or with alcoholic alkali solution in accordance with the following formula scheme:

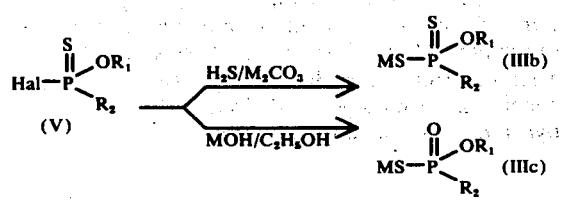

in which

Hal, $R_1$, $R_2$ and M have the meanings indicated earlier.

The following may be mentioned as examples of compounds of the formula (III): the sodium salts and potassium salts of O-methyl-S-methyl-, O-methyl-S-ethyl-, O-methyl-S-n-propyl-, O-methyl-S-iso-propyl-, O-methyl-S-n-butyl-, O-methyl-S-tert.-butyl-, O-methyl-S-sec.-butyl-, O-ethyl-S-methyl-, O-ethyl-S-ethyl-, O-ethyl-S-n-propyl-, O-ethyl-S-iso-propyl-, O-ethyl-S-n-butyl-, O-ethyl-S-sec.-butyl-, O-ethyl-S-isobutyl-, O-ethyl-S-tert.-butyl-, O-n-propyl-S-methyl-, O-n-propyl-S-ethyl-, O-n-propyl-S-n-propyl-, O-n-propyl-S-isopropyl-, O-n-propyl-S-n-butyl-, O-n-propyl-S-iso-butyl-, O-n-propyl-S-tert.-butyl-, O-n-butyl-S-methyl-, O-n-butyl-S-ethyl-, O-n-butyl-S-n-propyl-, O-n-butyl-S-isopropyl-, O-n-butyl-S-n-butyl-, O-n-butyl-S-sec.-butyl-, O-n-butyl-S-tert.-butyl-, O-iso-butyl-S-methyl-, O-iso-butyl-S-ethyl-, O-sec.-butyl-S-ethyl-, O-sec.-butyl-S-n-propyl- and O-tert.-butyl-S-ethyl-(thiono)-dithiolphosphoric acid ester; also O-methyl-N-methyl-, O-methyl-N-ethyl-, O-methyl-N-n-propyl-, O-methyl-N-iso-propyl-, O-methyl-N-n-butyl-, O-methyl-N-iso-butyl-, O-methyl-N-sec.-butyl-, O-methyl-N-tert.-butyl-, O-ethyl-N-methyl-, O-ethyl-N-ethyl-, O-ethyl-N-n-propyl-, O-ethyl-N-iso-propyl-, O-ethyl-N-n-butyl-, O-ethyl-N-iso-butyl-, O-ethyl-N-sec.-butyl-, O-ethyl-N-tert.-butyl-, O-n-propyl-N-methyl-, O-n-propyl-N-ethyl-, O-n-propyl-N-n-propyl-, O-n-propyl-N-iso-propyl-, O-n-propyl-N-n-butyl-, O-n-propyl-N-iso-butyl-, O-n-propyl-N-sec.-butyl-, O-n-propyl-N-tert.-butyl-, O-iso-propyl-N-methyl-, O-iso-propyl-N-ethyl-, O-iso-propyl-N-n-propyl-, O-iso-propyl-N-iso-propyl-, O-iso-propyl-N-n-butyl-, O-iso-propyl-N-sec.-butyl-, O-iso-propyl-N-tert.-butyl-, O-n-butyl-N-methyl-, O-n-butyl-N-ethyl-, O-n-butyl-N-n-propyl-, O-n-butyl-N-iso-propyl-, O-n-butyl-N-n-butyl, O-n-butyl-N-iso-butyl-, O-n-butyl-N-sec.-butyl-, O-n-butyl-N-tert.-butyl-, O-iso-butyl-N-methyl-, O-iso-butyl-N-ethyl-, O-iso-butyl-N-n-propyl-, O-iso-butyl-N-n-iso-propyl-, O-tert.-butyl-N-methyl-, O-tert.-butyl-N-ethyl-, O-tert.-butyl-N-n-propyl-, O-tert.-butyl-N-n-butyl-, O-methyl-N-allyl-, O-methyl-N-propargyl-, O-methyl-N-butenyl-, O-ethyl-N-allyl-, O-ethyl-N-propargyl-, O-ethyl-N-butenyl-, O-n-propyl-N-allyl, O-n-propyl-N-propargyl-, O-n-propyl-N-butenyl-, O-n-butyl-N-allyl- and O-n-butyl-N-propargyl-(thiono)-thiolphosphoric acid esteramide and the corresponding N,N-disubstituted amides.

The reaction according to the invention is preferably carried out in the presence of a solvent which term includes a mere diluent. Practically all inert organic solvents can be used for this purpose. These include, in particular, aliphatic and aromatic optionally chlorinated hydrocarbons, such as benzene, toluene, xylene, benzine, methylene chloride, chloroform, carbon tetrachloride or chlorobenzene; ethers, such as diethyl ether, dibutyl ether and dioxane; ketones, such as acetone, methyl ethyl ketone, methyl isopropyl ketone and methyl isobutyl ketone; nitriles, such as acetonitrile and propionitrile; and amides, such as dimethylformamide.

The reaction temperature can be varied within a wide range. In general, the reaction is carried out at 0° to 100° C, preferably at 25° to 60° C, and the reaction is usually allowed to take place under normal pressure.

If desired, the phosphoric acid salt (III) is employed in a slight excess when carrying out the process.

In general, a mixture of the starting components (II) and (III) in one of the solvents indicated is heated, for one or several hours, to the indicated temperatures. After cooling, the reaction mixture is poured into toluene and the organic phase is then worked up in the usual manner, for example by washing, drying and distillation.

The new compounds are mostly obtained in the form of oils which can in some cases not be distilled without decomposition, but can be freed from the last volatile constituents by so-called "slight distillation," that is to say by prolonged heating under reduced pressure to moderately elevated temperatures, and can be purified in this way. They are characterized by their refractive indexes. Some of the products are obtained in a crystalline form; in that case, they can be characterized by their melting points.

As already mentioned, the S-[1,6-dihydro-3-methyl-6-oxo-pyridazin-(1)-ylmethyl]-(thiono)-(di)-thiolphosphoric acid ester and ester-amide derivatives according to the invention are distinguished by an outstanding nematocidal activity, especially against nematodes which damage plants. Some compounds in addition exhibit an insecticidal, acaricidal and/or fungicidal action.

For this reason, the compounds according to the invention can be employed successfully in plant protection.

The active compounds according to the invention couple a low toxicity towards warm-blooded animals with powerful nematocidal properties and can therefore be used for combating nematodes, especially phytopathogenic nematodes. These essentially comprise leaf nematodes (Aphelenchoides), such as the chrysanthemum eelworm (A. ritzemabosi), the leaf-blotch eelworm (A. fragariae) and the rice eelworm (A. oryzae); stem nematodes (Ditylenchus), such as the stem eelworm (D. dipsaci); root-knot nematodes (Meloidogyne), such as M. arenaria and M. incognita; cyst-forming nematodes (Heterodera), such as the potato cyst eelworm (H. rostochiensis) and the beet cyst eelworm (H. schachtii); as well as root nematodes which exist free, for example of the genera Pratylenchus, Paratylenchus, Rotylenchus, Xiphinema and Radopholus.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e., calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other nematocides, insecticides, acaricides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. nematodes, insects, acarids and fungi, and more particularly methods of combating nematodes, which comprises applying to at least one of correspondingly (a) such nematodes, (b) such insects, (c) such acarids, (d) such fungi, and (e) the corresponding habitat thereof, i.e., the locus to be protected, e.g. to a growing crop, to an area where a crop is to be grown or to a domestic animal, a correspondingly combative or toxic amount, i.e., a nematocidally, insecticidally, acaricidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Critical concentration test

Test nematode: *Meloidogyne incognita*, Solvent: 3 parts by weight of acetone, Emulsifier: 1 part by weight of alkylarylpolyglycol ether.

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in p.p.m., was decisive. The soil was filled into pots, lettuce was sown in and the pots were kept at a greenhouse temperature of 27° C. After 4 weeks, the lettuce roots were examined for infestation with nematodes, and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compounds, the amounts applied and the results can be seen from Table 1 in which the compounds according to the invention are numbered in accordance with the corresponding preparative Examples.

Table 1

| Active compound (structure) | Nematodes/Meloidogyne incognita Degree of destruction in % at active compound concentrations in ppm of | | | | |
|---|---|---|---|---|---|
| | 20 | 10 | 5 | 2.5 | 1.25 |
| 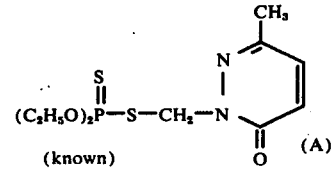 (A) (known) | 100 | 98 | 80 | 0 | |
| 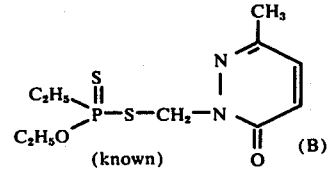 (B) (known) | 0 | | | | |
| 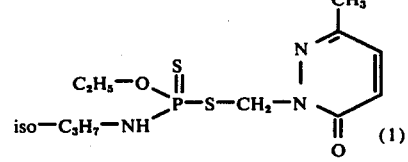 (1) | 100 | 100 | 100 | 100 | 98 |
| 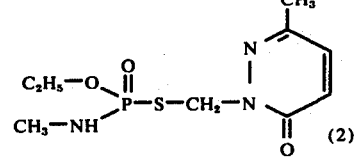 (2) | 100 | 100 | 99 | 80 | 50 |
| 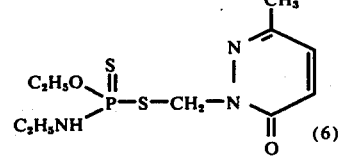 (6) | 100 | 100 | 99 | 99 | 98 |
| 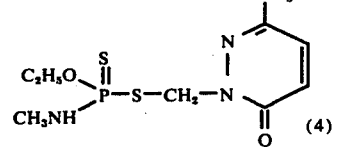 (4) | 100 | 100 | 100 | 99 | 90 |

EXAMPLE 2 a) 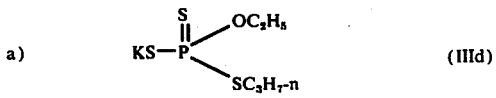 (IIId)

190 g of hydrogen sulfide were introduced over the course of 2 hours into a suspension of 280 g of potassium carbonate and 1.5 liters of acetonitrile at 0° to 10° C, 218.5 g (1 mole) of O-ethyl-S-n-propyl-thionothiolphosphoric acid ester chloride were then added dropwise to the reaction mixture over the course of 20 minutes at the same temperature and the mixture was then stirred for a further 18 hours, at room temperature. A further 50 g of H₂S were then introduced at 0° to 10° C. Thereafter, the batch was stirred for 48 hours at room temperature, the precipitate which had separated out was then filtered off and the filter residue was boiled with 1.5 liters of acetone. After renewed filtration, the combined filtrates were freed from the solvent under reduced pressure. On addition of ether, 125 g (50% of theory) of the salt of the above formula crystallized out.

b) (IIIe)

560.0 g (4.05 moles) of anhydrous, powdered potassium carbonate were suspended in 1,500 cc of acetonitrile. Hydrogen sulfide was introduced into this suspension for 30 minutes at 0° to 5° C and 403.4 g (2.0 moles) of O-ethyl-N-mono-isopropylamido-thionophosphoric acid chloride were added dropwise to the mixture, at the stated temperature, while introducing further gas. Hydrogen sulfide was then passed in very slowly for a further 10 hours and finally the batch was stirred overnight at room temperature after discontinuing the stream of gas. The reaction mixture was filtered and the residue was rinsed with a little acetonitrile. Concentration of the combined filtrates gave a colorless salt which was freed from organic impurities by extraction by stirring with anhydrous ether. After drying in a desiccator, 334.6 g (70.4% of theory) of the potassium salt of O-ethyl-N-monoisopropylamido-dithiophosphoric acid were obtained as colorless crystals of melting point 156° C, in agreement with German Published Specification DOS No. 2,035,073.

The following salts were prepared analogously:

(IIIf)

(IIIa)

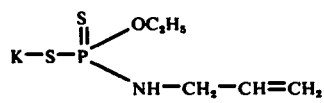

c)

(IIIg)

(IIIh)

O-Ethyl-N-ethyl-thionophosphoric acid ester-amide-halide was dissolved in 50/50 ethanol/water by volume, and a 10% solution of potassium hydroxide in water was added at 40° C. The batch was stirred additionally and was worked up as described in German Published Specification DAS 1,080,109 although it could be directly used in further reaction.

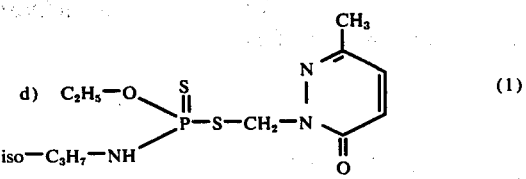

d) (1)

A mixture of 15.8 g (0.1 mole) of 1,6-dihydro-1-chloromethyl-3-methyl-6-oxo-pyridazine and 26.2 g (0.11 mole) of the potassium salt of O-ethyl-N-isopropylthionothiolphosphoric acid ester-amide in 200 ml of acetonitrile was heated to 50° C for 3 hours. The reaction mixture was then cooled to 20° C and poured into 500 ml of toluene. The toluene solution was washed with saturated sodium bicarbonate solution and water, dried over sodium sulfate and then evaporated. 18 g (56% of theory) of O-ethyl-N-isopropyl-S-[1,6-dihydro-3-methyl-6-oxo-pyridazin-(1)-ylmethyl]-thionothiolphosphoric acid ester-amide were obtained as a yellow oil of refractive index $n_D^{25}$: 1.5752.

e. The compounds of the formula (I) listed below were prepared analogously to Example 1 (d) using suitable starting materials prepared as in Example 1 (a), (b) or (c):

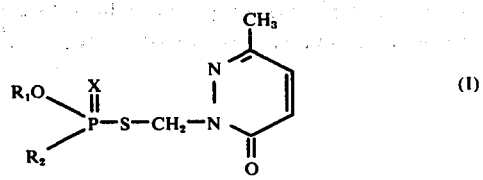

(I)

| Compound | $R_1$ | $R_2$ | X | Melting point; refractive index | Yield (% of theory) |
|---|---|---|---|---|---|
| 2 | $C_2H_5$ | $NH-CH_3$ | O | 95° C | 54 |
| 3 | $C_2H_5$ | $NH-CH_2-CH=CH_2$ | S | $n_D^{23}$: 1.5829 | 52 |
| 4 | $C_2H_5$ | $NH-CH_3$ | S | $n_D^{23}$: 1.5808 | 43 |
| 5 | $C_2H_5$ | $SC_3H_7-n$ | S | $n_D^{23}$: 1.5810 | 54 |
| 6 | $C_2H_5$ | $NH-C_2H_5$ | S | 59° C | 54 |
| 7 | $C_2H_5$ | $N(CH_3)_2$ | O | $n_D^{24}$: 1.5257 | 36 |
| 8 | $C_3H_7-n$ | $NH-C_3H_7-iso$ | S | $n_D^{24}$: 1.5604 | 66 |
| 9 | $C_2H_5$ | $NH-C_4H_9-sec$ | O | partially crystalline | 46 |
| 10 | $C_3H_7-n$ | $NH-C_2H_5$ | S | $n_D^{24}$: 1.5632 | 79 |
| 11 | $C_3H_7-iso$ | $NH-C_2H_5$ | S | $n_D^{24}$: 1.5625 | 69 |

Other compounds which can be similarly prepared include:
O-methyl-S-methyl-S-[1,6-dihydro-3-methyl-6-oxo-pyridazin-(1)-ylmethyl]-dithiolphosphoric acid ester,
O-isobutyl-N-propargyl-S-1,6-dihydro-3-methyl-6-oxo-pyridazin-(1)-ylmethyl]-thiolphosphoric acid ester-amide,
O-butyl-N,N-di-isopropyl-S-[1,6-dihydro-3-methyl-6-oxo-pyridazin-(1)-ylmethyl]-thionothiolphosphoric acid ester-amide,
and the like.

What is claimed is:

1. An S-[1,6-dihydro-3-methyl-6-oxo-pyridazin-(1)-ylmethyl]-(thiono)-(di)-thiol-phosphoric acid ester or ester-amide of the formula

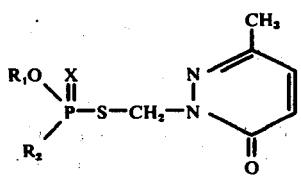

in which
R₁ is alkyl with up to 6 carbon atoms,
R₂ is monoalkylamino, dialkylamino, alkenylamino or alkynylamino with up to 6 carbon atoms per alkyl, alkenyl or alkynyl moiety, and
X is oxygen or sulfur.

2. A compound according to claim 1 in which R₁ has up to 4 carbon atoms and R₂ has up to 4 carbon atoms per alkyl, alkenyl or alkynyl moiety.

3. A compound according to claim 1 in which R₁ is ethyl, n-propyl or isopropyl.

4. The compound according to claim 1 wherein such compound is O-ethyl-N-isopropyl-S-[1,6-dihydro-3-methyl-6-oxo-pyridazin-(1)-ylmethyl]-thionothiol-phosphoric acid ester-amide of the formula 5. The compound according to claim 1 wherein such compound is O-ethyl-N-ethyl-S-[1,6-dihydro-3-methyl-6-oxo-pyridazin-(1)-ylmethyl]-thionothiol-phosphoric acid ester-amide of the formula 6. The compound according to claim 1 wherein such compound is O-ethyl-N-methyl-S-[1,6-dihydro-3-methyl-6-oxo-pyridazin-(1)-ylmethyl]-thionothiol-phosphoric acid ester-amide of the formula

* * * * *